United States Patent [19]

Sudo et al.

[11] Patent Number: 5,328,643
[45] Date of Patent: * Jul. 12, 1994

[54] OPTICALLY ACTIVE COMPOUNDS, LIQUID CRYSTAL COMPOSITION CONTAINING SAID COMPOUNDS, AND LIQUID CRYSTAL OPTICAL MODULATOR USING SAID COMPOSITION

[75] Inventors: Yuka Sudo, Kasama; Katsumi Kondo; Teruo Kitamura, both of Katsuta; Koichi Matsumura, Ibaraki; Mitsuru Kawada, Amagasaki; Yoshihiro Sugihara, Toyonaka, all of Japan

[73] Assignees: Takeda Chemical Industries, Ltd., Osaka; Hitachi, Ltd., Tokyo, both of Japan

[*] Notice: The portion of the term of this patent subsequent to Dec. 1, 2009 has been disclaimed.

[21] Appl. No.: 841,467

[22] Filed: Feb. 26, 1992

Related U.S. Application Data

[63] Continuation of Ser. No. 382,385, Jul. 20, 1989, abandoned.

[30] Foreign Application Priority Data

Jul. 20, 1988 [JP] Japan .................. 63-179029

[51] Int. Cl.$^5$ .................. C09K 19/12; C09K 19/20; C07C 69/76; C07C 41/00
[52] U.S. Cl. .................. 252/299.65; 252/299.6; 252/299.64; 252/299.66; 560/59; 560/73; 560/102; 560/108; 560/109; 560/141; 568/631; 568/642
[58] Field of Search .................. 252/299.01, 299.65, 252/299.66, 299.64, 292.6; 560/59, 73, 102, 108, 109, 141; 568/631, 642

[56] References Cited

U.S. PATENT DOCUMENTS

| | | | |
|---|---|---|---|
| 4,650,600 | 3/1987 | Heppke et al. | 252/299.01 |
| 5,013,475 | 5/1991 | Shibata et al. | 252/299.66 |
| 5,100,579 | 3/1992 | Higuchi et al. | 252/299.65 |
| 5,130,048 | 7/1992 | Wand et al. | 252/299.65 |
| 5,152,919 | 10/1992 | Kitamura et al. | 252/299.65 |
| 5,167,855 | 12/1992 | Wand et al. | 252/299.66 |
| 5,167,863 | 12/1992 | Kitamura et al. | 252/299.65 |

FOREIGN PATENT DOCUMENTS 0138006  4/1985  European Pat. Off.
0257457  3/1988  European Pat. Off.

OTHER PUBLICATIONS

Tetrahedron Letters, No. 6, pp. 419–422.
Tetrahedron Letters, vol. 37, No. 12, pp. 2249–2254.

*Primary Examiner*—Philip Tucker
*Attorney, Agent, or Firm*—Antonelli, Terry, Stout & Kraus

[57] ABSTRACT

The invention relates to optically active compounds represented by the general formula I $$R_1-Q_1-M-Q_2-\overset{*}{C}H-\overset{*}{C}H-CH_2-Q_3-R_4 \quad [I]$$
$$\qquad\qquad\qquad\;\; |\quad\; |$$
$$\qquad\qquad\qquad\; R_2\;\; R_3$$

wherein $R_1$, $R_2$, $R_3$, $R_4$, $Q_1$, $Q_2$, $Q_3$, and M are defined as in the specification, methods and intermediates for their preparation, liquid crystal compositions comprising at least one optically active compound of formula I and their use in electrooptical display, switching and modulation devices.

15 Claims, 1 Drawing Sheet

EXAMPLE OF LIQUID CRYSTAL DEVICE
(SCHEMATIC ILLUSTRATION)

EXAMPLE OF LIQUID CRYSTAL DEVICE
(SCHEMATIC ILLUSTRATION)

OPTICALLY ACTIVE COMPOUNDS, LIQUID CRYSTAL COMPOSITION CONTAINING SAID COMPOUNDS, AND LIQUID CRYSTAL OPTICAL MODULATOR USING SAID COMPOSITION

This application is a continuation application of application Ser. No. 382,385, filed Jul. 20, 1989, now abandoned.

BACKGROUND OF THE INVENTION

1. Field of the Invention

The present invention relates to optically active compounds and liquid crystal compositions comprising these compounds. The compounds and compositions of the present invention show a ferroelectric liquid crystal phase, and accordingly are useful as electrooptic switching elements such as liquid crystal display devices or the like, and can be used in liquid crystal optical modulators.

2. Related Art Statement

Liquid crystal display devices have various excellent features such as low-voltage operability, low power consumption, being thin and light-weight, being a non-emissive type and easy on the eye, etc. Accordingly, they are in wide use as various display devices.

Liquid crystal display devices using a nematic liquid crystal operating in the so-called twisted nematic mode (TN mode) are in use currently. However, display devices using this kind of nematic liquid crystals have the drawback of being very slow in response as compared to luminescent type display devices such as CRT, EL and the like. Consequently, when such display devices are applied in a display device, particularly a large scale display device capable of displaying a large amount of information, it is impossible to obtain a display of good contrast. Thus the liquid crystal display devices using a nematic liquid crystal have only a very limited applicability. There has recently been developed a liquid crystal display device using a nematic liquid crystal operating in the so-called super twisted nematic mode (STN mode) or SBE and capable of giving a display of improved contrast. Even in this STN mode liquid crystal display device, however, the response is not sufficient, and therefore said device finds also only a very limited application, because it cannot be used for displays capable of displaying a still larger amount of information. Hence, various attempts have been made to develop a new liquid crystal display system giving an excellent response.

Ferroelectric liquid crystals have a memory characteristics and give a high speed response, and accordingly their application to large scale displays is highly expected. As liquid crystals having retroelectric properties, there are known those showing a chiral smectic C phase, a chiral smectic H phase, a chiral smectic J phase, etc. Of these ferroelectric liquid crystals, those showing a chiral smectic C phase are thought to have highest practical utility.

Ferroelectric liquid crystals showing a chiral smectic C phase were first synthesized in 1975 by R. B. Meyer et al.; one typical example thereof is 2-methylbutyl 4-(4'-n-decyloxybenzylideneamino)cinnamate (hereinafter abbreviated to DOBAMBC) [J. Physique, 36, L69 (197.5)].

A thin film liquid crystal cell was prepared using DOBAMBC and was found to have a high speed response in the order of $\mu s$ [N. A. Clark et al., Appl. Phys. Lett., 36, 89 (1980)]. Since that time, there was started the development of optical modulation devices (e.g. liquid crystal display devices, photo-printer heads) using a ferroelectric liquid crystal showing a chiral smectic C phase (hereinafter may be referred to simply as "ferroelectric liquid crystal").

As a result, a number of ferroelectric liquid crystal compounds showing a chiral smectic C phase have been developed since then, and various ferroelectric liquid crystal compounds are already known. However, no ferroelectric liquid crystal compound is found yet which has satisfactory reliability and capability for use in display devices, particularly large scale displays, etc.

In order for a ferroelectric liquid crystal to be practically used in a liquid crystal display device, etc., the liquid crystal must be superior in high speed response, orientation, memory characteristics, characteristics of threshold voltage, temperature dependences of these properties, etc. Also, the ferroelectric liquid crystal is required to show a chiral smectic C phase over a wide temperature range so that it can operate within a sufficiently wide temperature range including room temperature, and further to have excellent physical and chemical stabilities.

In order for a ferroelectric liquid crystal to have, in particular, excellent physical and chemical stabilities, good high speed response and good memory characteristics, the liquid crystal must have a large spontaneous polarization.

Among the so far developed ferroelectric liquid crystals, no compound is found yet which satisfies all the above requirements. For example, the above mentioned DOBAMBC, being a liquid crystal of Schiff's base type, is insufficient in chemical stability to water, light, etc., and moreover, has a small spontaneous polarization of 4 $nC/cm^2$ or below.

Ester type liquid crystals are reported as being ferroelectric liquid crystals which are chemically stable. However, these liquid crystals are not satisfactory because they have no sufficiently large spontaneous polarization and no sufficiently wide temperature range of chiral smectic C phase.

In order to obtain a large spontaneous polarization, there were synthesized compounds having two asymmetric carbon atoms as an optically active group essential for the expression of a chiral smectic C phase.

These compounds include, for example, liquid crystal compounds having a dichiral epoxide side chain [David M. Walba et al., Journal of American Chemical Society, 108, 7424 (1986)], and liquid crystal compounds having a halogen atom and a methyl group on two adjacent asymmetric carbon atoms [cf. e.g. JP-A-168780/1985, 18358/1985, 68449/1986, 40/1987, 46/1987, 103043/1987, 111950/1987, 142131/1987, 175443/1987].

A typical example of the above liquid crystal compounds is ( s)-2-chloro-3-methylbutyl 4'-octylcarbonyloxy-4-biphenylcarboxylate [JP-A-68449/1986 ]. This liquid crystal compound has a very large spontaneous polarization of 180 $nC/cm^2$ but, being an aliphatic chloro compound, has poor chemical stability. Hence, there was synthesized 4'-octylcarbonyloxy-4-[(s)-2-methoxy-(s)-3-methylpentyloxycarbonyl]biphenyl [JP-A-28036/1987]. This compound has excellent chemical stability but has an insufficient spontaneous polarization of 17 $nC/cm^2$.

SUMMARY OF THE INVENTION

The present inventors made investigation in order to find out a ferroelectric liquid crystal compound having excellent physical and chemical stabilities and a large spontaneous polarization and have reached the present invention. That is, the present inventors made investigation on liquid crystal compounds wherein a chemically stable ester compound and an optically active group having two asymmetric carbon atoms are combined, and have reached the present invention.

Specifically, the present inventors succeeded in converting optically active groups having two asymmetric carbon atoms to a structure containing no halogen-carbon bond of poor chemical stability and then bonded said structure to a 6-membered ring (e.g. benzene ring) which is to constitute the skeleton of a liquid crystal compound to be obtained and to an alkyl group which is to become a terminal group of said compound, in a particular pattern; and consequently, the present invention has been achieved.

DETAILED DESCRIPTION OF PREFERRED EMBODIMENTS

Figure 1:
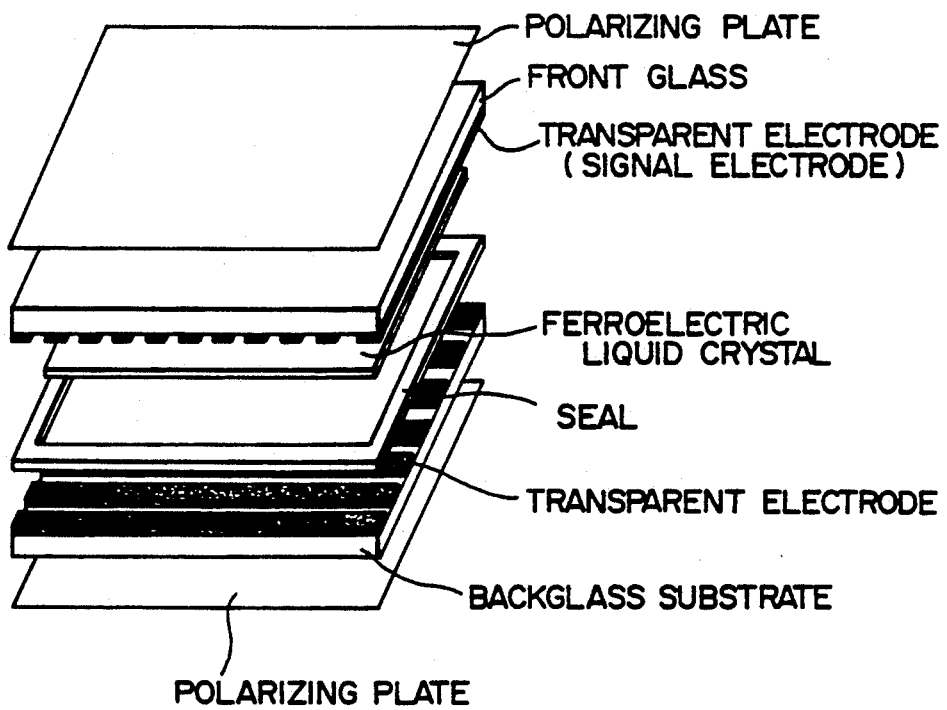
FIG. 1 is a schematic illustration of an example of a liquid crystal display device using the liquid crystal compositions of the present invention.

The first aspect of the present invention relates to optically active compounds represented by the general formula I:

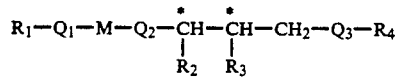

wherein $R_1$ is an alkyl group of 3-14 carbon atoms; $R_2$ and $R_3$, which may be the same or different, are independently a lower alkyl group of 1-3 carbon atoms; $R_4$ is an alkyl group of 1-10 carbon atoms; $Q_1$ is a single bond, an ether group, a carboxylic acid ester group, a carbonyl group or a carbonyldioxy group; $Q_2$ and $Q_3$ are independently an ether group, a carboxylic acid ester group or a carbonyl group; M is

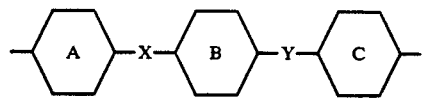

or

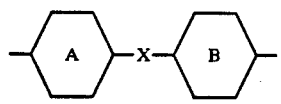

X and Y are independently a single bond, a carboxylic acid ester group, a methyleneoxy group or an ethylene group, and

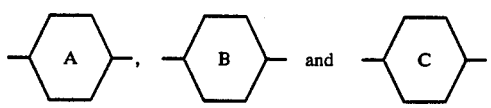

are independently a homocyclic or heterocyclic six-membered ring-1,4-diyl group which may contain 1-2 oxygen or nitrogen atoms as ring-forming atoms); the carbon atoms with the asterisk (*) denote asymmetric carbon atoms.

The second aspect of the present invention relates to dichiral alcohols represented by the general formula [III] which are useful as a raw material constituting the dichiral portion of the compounds of the general formula [I]

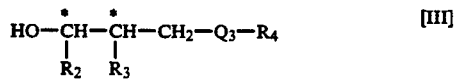

wherein $R_2$, $R_3$, $R_4$ and $Q_3$ have the same definitions as given above.

The third aspect of the present invention relates to liquid crystal compositions comprising at least one of the above optically active compounds.

The fourth aspect of the present invention relates to liquid crystal optical modulators comprising the above liquid crystal composition.

These aspects are explained below, starting with the first aspect.

The compound I of the present invention can be classified into the following compounds I' and I" depending upon the basic skeleton M.

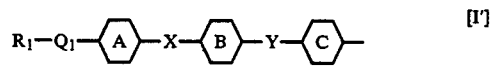

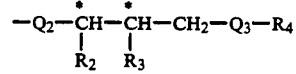

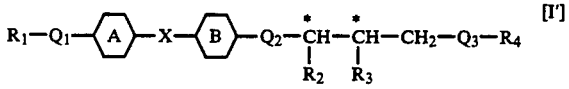

In the above compounds I, I' and I" the alkyl group of 3-14 carbon atoms represented by $R_1$ can be of straight chain or branched chain. Specifically, there can be mentioned straight chain alkyl groups such as propyl, butyl, pentyl, hexyl, heptyl, octyl, nonyl, decyl, undecyl, dodecyl, tridecyl, tetradecyl and the like, as well as branched chain alkyl groups such as isopropyl, isobutyl, sec-butyl, tert-butyl, isopentyl, neopentyl, tert-pentyl, isohexyl, 1-methylpentyl, 2-methylpentyl, 5-methylhexyl, 2,3,5-trimethylhexyl, 2,7,8-trimethyldecyl, 4-ethyl-5-methylnonyl and the like. Of these, preferable are straight chain alkyl groups of 6-12 carbon atoms, such as hexyl, heptyl, octyl, decyl, undecyl, dodecyl and the like. As the lower alkyl groups of 1-3 carbon atoms represented by $R_2$ and $R_3$, there can be mentioned straight or branched chain alkyl groups such as methyl, ethyl, propyl, isopropyl and the like. Of these, methyl is preferable. The alkyl group of 1-10 carbon atoms represented by $R_4$ can be of straight chain or branched chain. Specifically, there can be mentioned straight chain alkyl groups such as methyl, ethyl, propyl, butyl, pentyl, hexyl, heptyl, octyl, nonyl, decyl and the like, as well as branched chain alkyl groups such as isopropyl, isobutyl, sec-butyl, tert-butyl, isopentyl, neopentyl, tert-pentyl, isohexyl, 1-methylpentyl, 2-methylpentyl, 5-methylhexyl, 4-ethylhexyl, 2,3,5-trimethylhexyl, 4-ethyl-5-methylhexyl and the like. Of these, preferable are straight chain alkyl groups of 1-8 carbon atoms such as methyl, ethyl, propyl, butyl, pentyl, heptyl and octyl. As the carboxylic acid ester groups represented by $Q_1$, $Q_2$ and $Q_3$, there can be mentioned an ester group represented by

and an ester group represented by

With respect to the various bond and groups which can be taken by $Q_1$, $Q_2$ and $Q_3$, it is preferable $Q_1$ be a single bond or an ether group, $Q_2$ be an ether group a

ester group or a

ester group and $Q_3$ be an ether group.

As the carboxylic acid ester groups represented by X and Y, there can be mentioned a

ester group and a

ester group. As the methyleneoxy group represented by X and Y, there can be mentioned —CH$_2$—O— and —OCH$_2$—.

The six-membered ring-1,4-diyl groups represented by

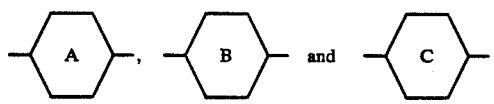

denote six-membered rings having two bonds at the para positions, and there can be specifically mentioned, for example, p-phenylene, 1,4-cyclohexylene, 2,5-(1,3-dioxane)diyl, 2,5-pyridinediyl, 2,5-pyrimidinediyl, 2,5-(1,4-pyrazine)diyl and 3,6-(1,2-pyridazine)diyl. These rings may be substituted with a halogen, cyano, methyl or methoxy group.

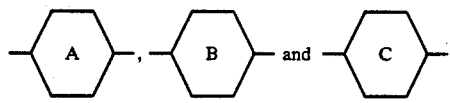

may be the same or different.

2,5-(1,3-Dioxane)diyl can be

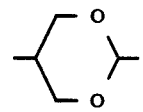

or

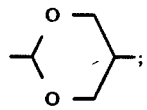

2,5-pyridinediyl can be

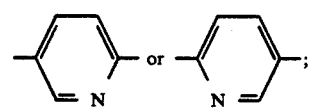

2,5-pyrimidinediyl can be

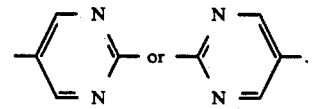

When M is

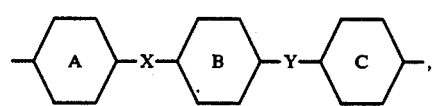

preferable combinations of A, B, C, X and Y include the case where one of X and Y is a single bond, the other of them is a carboxylic acid ester bond, and all of

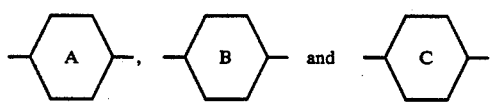

are p-phenylene. When M is

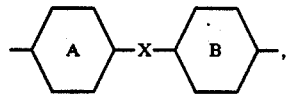

preferable combinations of A, B and X include the case where X is a single bond or a carboxylic acid ester bond and both of

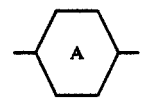

and

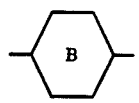

are p-phenylene.

The compounds I have two asymmetric carbon atoms within the molecule and therefore have four different optical isomers, that is, (R,R) type, (R,S) type, (S, R) type and (S, S) type.

The optically active compounds I of the present invention have a structure in which each symmetric carbon atom bonds to oxygen or carbonyl, and therefore the compounds generally show high spontaneous polarization. In addition, most of the compounds I show a chiral smectic C (Sc*) phase which is a liquid crystal phase suitable for display methods utilizing the ferroelectric properties of liquid crystals, and the temperature range of the chiral smectic C phase is low and wide.

The optically active compounds of the present invention are very stable to heat, light, water and air. Accordingly, in putting the compounds to practical use as liquid crystal materials, there can be eliminated inconveniences such as arrangements of an apparatus for prevention of overheating, a glass frit seal for prevention of moisture absorption or permeation, etc.

The optically active compounds I of the present invention have excellent compatibility with conventionally known liquid crystal compounds such as those of Schiff's base type, biphenyl type, phenylcyclohexane type, heterocyclic type and the like. Therefore, the compounds can be made into liquid crystal compositions having excellent properties, by incorporating them into said liquid crystal compounds.

As the liquid crystal compounds into which the optically active compounds I of the present invention can be incorporated, there can be mentioned, for example, ferroelectric liquid crystal compounds as well as liquid crystal compounds showing a smectic C phase. The ferroelectric liquid crystal compounds include, for example, biphenyl type liquid crystals described in JP-A-118744/1984 and 13729/1985, ester type liquid crystals described in JP-A-128357/1984, 51147/1985, 22051/1986 and 249953/1986, and pyrimidine type liquid crystals described in JP-A-260564/1985, 24756/1986, 85368/1986 and 215373/1986. The liquid crystal compounds showing a smectic C phase include, for example, ester type liquid crystal compounds described in JP-A-228036/1987, and cyclohexane type liquid crystals and heterocyclic type liquid crystals described in the materials of the 16th Freiburg Liquid Crystal Forum (Mar. 21, 1986) and the materials of the First International Symposium on Ferroelectric Liquid Crystals (Sep. 21, 1987).

The ferroelectric liquid crystal compounds of the present invention can also be incorporated into the nematic or cholesteric liquid crystals described in "Flüssige Kristalle in Tabellen" I & II, VEB-Verlag, Leipzig, and further can be mixed with any commercially available nematic liquid crystal compound. When the ferroelectric liquid crystal compounds of the present invention are incorporated into nematic liquid crystals to utilize the chirality of the former, the twisting direction of the cholesteric pitch and the pitch length of the nematic liquid crystal compositions obtained can be freely controlled via the amount added.

The optically active compounds I of the present invention can be produced by various processes shown below.

PROCESS I

Compounds of the general formula I wherein $Q_2$ bonding the skeletal component and the dichiral side chain component is a

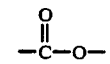

ester group.

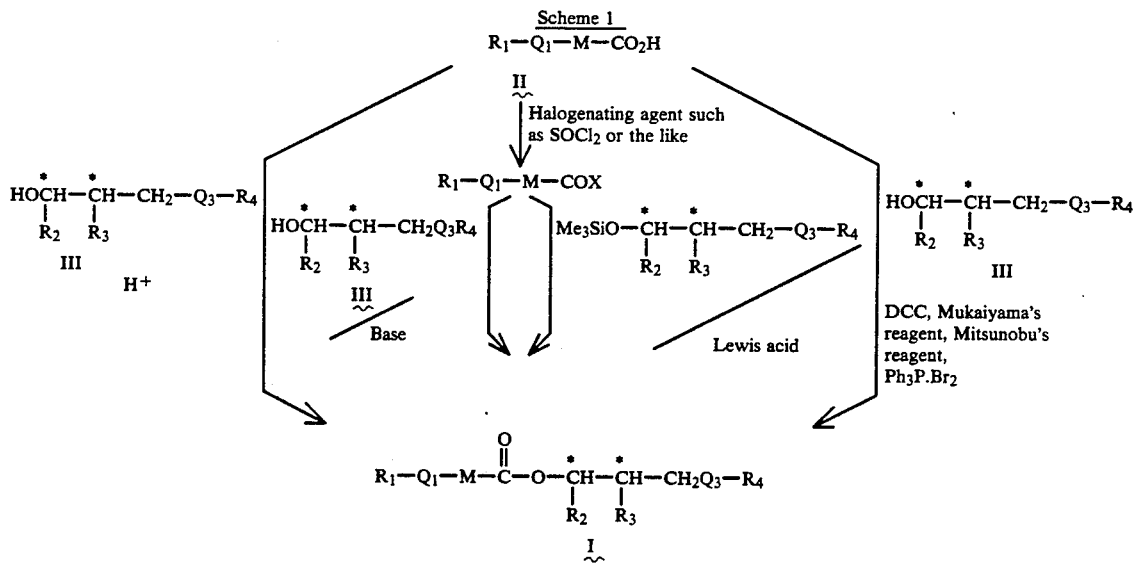

[In the scheme 1, $R_1$, $R_2$, $R_3$, $R_4$, $Q_1$, $Q_3$, M and the asterisk (*) have the same definitions as given above, and X is a halogen atom.]

As shown in the above scheme 1, the compound I can be obtained by subjecting a carboxylic acid II (which is to later constitute the basic skeleton of the compound I)

and an optically active dichiral alcohol III to a condensation reaction. This condensation reaction can be effected according to a conventional method. That is, the carboxylic acid II and the optically active dichiral secondary alcohol III are subjected to a dehydrating condensation reaction in an organic solvent in the presence of a proton acid to obtain a compound I. As the organic solvent, there can be mentioned, for example, hydrocarbons such as hexane, benzene, toluene and the like, halogenated hydrocarbons such as chloroform, methylene chloride, carbon tetrachloride, 1,2-dichloroethane and the like, ethers such as diethyl ether, tetrahydrofuran, dioxane and the like, ethyl acetate, acetonitrile and dimethylformamide.

The thus produced optically active compound I can be isolated from the reaction mixture and purified according to ordinary separation and purification methods (e.g. extraction, solvent operation, column chromatography, liquid chromatography, recrystallization, fractional crystallization). The optically active compound I can also be produced at a high purity by converting the carboxylic acid II to an acid halide with a halogenating agent such as thionyl chloride, thionyl bromide or the like, subjecting the acid halide to an esterification reaction with the optically active dichiral secondary alchol III in an organic solvent in the presence of an organic base such as pyridine, triethylamine or the like at a low temperature, room temperature or an elevated temperature for several hours or, depending upon the case, several days, and subjecting the resulting esterification product to an ordinary separation and purification procedure.

The condensation reaction of the Process 1 can also be effected by appropriately selecting a method other than those mentioned above, such as a method using an activating agent [e.g. N,N'-dicyclohexylcarbodiimide (DCC), a Mukaiyama's reagent, i.e. a 1-methyl-2-halopyridinium iodide, diethyl azodicarboxylate (DEAD) and triphenylphosphine (Mitsunobu's reagent), triphenylphosphine dibromide] or a method comprising converting the carboxylic acid II to an acid halide with a halogenating agent (e.g. thionyl chloride, thionyl bromide) and then condensing the halide with a trimethylsilyl ether derivative of the optically active dichiral secondary alcohol III in the presence of a catalytic amount of a Lewis acid (e.g. zinc chloride).

PROCESS 2

Compounds of the general formula I wherein $Q_2$ bonding the skeletal component and the dichiral component is a —O— ether group.

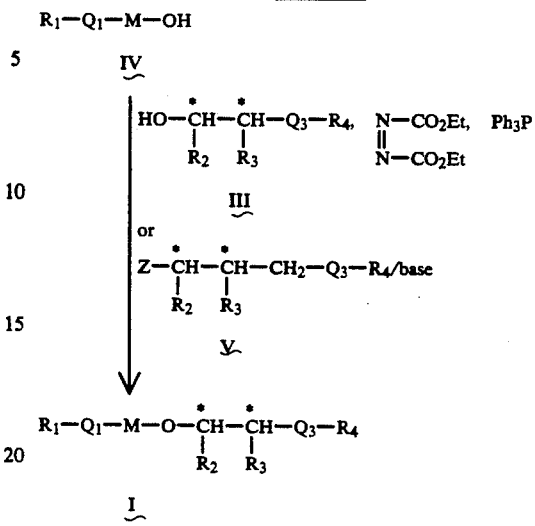

Scheme 2

[In the scheme 2, $R_1$, $R_2$, $R_3$, $R_4$, $Q_1$, $Q_3$, M and the asterisk (*) have the same definitions as given above. Z in the formula V denotes a halogen atom, an organic sulfonyloxy group or the like.]

The compound I can be obtained by subjecting an alcohol or phenolic hydroxyl compound IV (which is to later constitute the skeletal portion of the compound I) and an optically active dichiral secondary alcohol III to a known condensation reaction. The compound I can be obtained, for example, by the above mentioned condensation reaction using diethyl azodicarboxylate (DEAD) and triphenylphosphine ($Ph_3P$), or by a method comprising reacting the dichiral secondary alcohol III with an organic sulfonyl chloride in an appropriate organic solvent in the presence of an organic base (e.g. pyridine, triethylamine) or an inorganic base (e.g. sodium hydride) to convert the alcohol III to a corresponding organic sulfonic acid ester, and then subjecting the ester to an etherification reaction with the alcohol or phenolic hydroxyl compound IV in the presence of an inorganic base (e.g. potassium carbonate, sodium hydride) or an organic base. As the organic sulfonyl chloride, there can be mentioned, for example, aromatic sulfonyl chlorides such as p-toluenesulfonyl chloride, o-toluenesulfonyl chloride, α-chlorobenzenesulfonyl chloride, benzenesulfonyl chloride, α-naphthalenesulfonyl chloride, β-naphthalenesulfonyl chloride and the like, as well as aliphatic sulfonyl chlorides such as methanesulfonyl chloride, trifluoromethanesulfonyl chloride and the like. As the organic solvent usable in the etherification reaction, there can be mentioned, for example, hydrocarbons, halogenated hydrocarbons, ethers (e.g. diethyl ether, tetrahydrofuran, dioxane), ethyl acetate, acetonitrile, dimethylformamide (DMF), dimethyl sulfoxide (DMSO) and hexamethylphosphoric triamide (HMPA). The activation of the optically active dichiral secondary alcohol III includes, besides the above conversion of the alcohol III to a corresponding organic sulfonic acid ester, the conversion of the alcohol III to a halide. The conversion of the optically active dichiral secondary alcohol III to a halide is effected, for example, by reacting the above mentioned organic sulfonic acid ester with a metal halide (e.g. sodium iodide, potassium iodide) or by reacting the dichiral secondary alcohol III directly with a halogenating agent (e.g. thionyl chloride, thionyl bromide). The thus obtained halide corresponding to the dichiral secondary alcohol III is subjected to an etherification reaction with the alcohol or phenolic hydroxyl compound IV in an organic solvent in the presence of an inorganic base (e.g. potassium carbonate, sodium hydride) or an organic base. The thus produced ether compound I can be isolated and purified from the reaction mixture by ordinary separation and purification means (e.g. extraction, solvent operation, column chromatography, liquid chromatography, recrystallization).

In the above, there were described the typical processes for producing the liquid crystal ester compounds I and liquid crystal ether compounds I of the present invention. However, the processes for producing the liquid crystal compounds I of the present invention are not restricted to the above mentioned processes comprising condensing the compound II or IV (which is to later constitute the basic skeletal portion of the compound I obtained) with the optically active dichiral secondary alcohol III or the optically active dichiral derivative V. For example, the compounds I can also be obtained by condensing a basic skeletal alcohol or phenolic hydroxyl compound having an optically active dichiral portion with other skeletal carboxylic acid or phenolic hydroxyl compound, or by condensing a basic skeletal carboxylic acid or a basic skeletal phenolic hydroxyl compound both having an optically active dichiral portion with other skeletal alcohol or phenolic hydroxyl compound.

Incidentally, the optically active dichiral alcohol III and optically active dichiral derivative V can be derived from optically active dichiral compounds which are easily available commercially as a reagent, and can also be obtained by a chemical asymmetric synthesis, a biological asymmetric synthesis using an enzyme or a microorganism, or an optical resolution. The thus obtained optically active dichiral secondary alcohol III can be subjected to inversion of configuration on asymmetric carbon by a chemical or biological method to convert it into other optical isomer(s). As the typical methods for inverting the hydroxyl group of optically active secondary alcohol, there are known, for example, a method in which the hydroxyl group is converted into an organic sulfonic acid ester and then subjected to an intermolecular nucleophilic substitution reaction to effect inversion, a method in which an optically active secondary alcohol is activated by N,N'-dicyclohexylcarbodiimide (DCC) in the presence of cuprous chloride and then reacted with an appropriate carboxylic acid to effect inversion, and a method in which an optically active secondary alcohol is reacted with diethyl azodicarboxylate (DEAD), triphenylphosphine ($Ph_3P$) and an appropriate carboxylic acid to effect inversion.

The optically active dichiral alcohol III which is a raw material of the important dichiral portion of the optically active compounds I of the present invention, is a novel compound and classified into three types depending upon the definition of $Q_3$. As the first type, there are mentioned those compounds of the general formula III wherein $Q_3$ is an ether group.

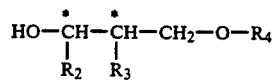

($R_2$ and $R_3$ are independently a lower alkyl group of 1-3 carbon atoms and $R_4$ is a straight chain or branched chain alkyl group of 1-10 carbon atoms.)

As typical examples of the first type, there are compounds of the above formula wherein $R_2$ and $R_3$ are both $CH_3$, i.e. optically active 4-alkyloxy-3-methyl-2-butanols.

These compounds, when $R_4$ is a straight chain alkyl group of 1-10 carbon atoms, specifically include optically active 4-methoxy-3-methyl-2-butanol, 4-ethoxy-3-methyl-2-butanol, 4-propoxy-3-methyl-2-butanol, 4-butoxy-3-methyl-2-butanol, 4-pentyloxy-3-methyl-2-butanol, 4-hexyloxy-3-methyl-2-butanol, 4-heptyloxy-3-methyl-2-butanol, 4-octyloxy-3-methyl-2-butanol, 4-nonyloxy-3-methyl-2-butanol, 4-decyloxy-3-methyl-2-butanol, etc.

When $R_4$ is a branched chain alkyl group of 1-carbon atoms, there are specifically mentioned optically active 4-isopropoxy-3-methyl-2-butanol, 4-isobutoxy-3-methyl-2-butanol, 4-tert-butoxy-3-methyl-2-butanol, 4-( 2-methylpentyloxy)-3-methyl-2-butanol, 4-( 3-methylpentyloxy)-3-methyl-2-butanol, etc.

Of these, preferable are compounds wherein $R_4$ is a straight chain alkyl group of 3-6 carbon atoms, specifically, 4-propoxy-3-methyl-2-butanol, 4-butoxy-3-methyl-2-butanol, 4-pentyloxy-3-methyl-2-butanol and 4-hexyloxy-3-methyl-2-butanol.

As the second type, there are mentioned those optically active dichiral secondary alcohols III wherein $Q_3$ is a

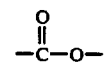

ester group.

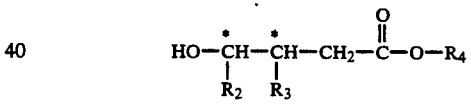

($R_2$ and $R_3$ are independently a lower alkyl group of 1-3 carbon atoms and $R_4$ is a straight chain or branched chain alkyl group of 1-10 carbon atoms.)

As typical examples of the second type, there are shown compounds of the above formula wherein $R_2$ and $R_3$ are both $CH_3$, i.e. optically active 4-hydroxy-3-methylpentanoic acid esters.

They specifically include optically active methyl 4-hydroxy-3-methylpentanoate, optically active ethyl 4-hydroxy-3-methylpentanoate, optically active propyl 4-hydroxy-3-methylpentanoate, optically active butyl 4-hydroxy-3-methylpentanoate, optically active pentyl 4-hydroxy-3-methylpentanoate, optically active hexyl 4-hydroxy-3-methylpentanoate, optically active heptyl 4-hydroxy-3-methylpentanoate, optically active octyl 4-hydroxy-3-methylpentanoate, optically active nonyl 4-hydroxy-3-methylpentanoate, optically active decyl 4-hydroxy-3-methylpentanoate and their corresponding esters of $C_{3-10}$ branched chain alcohols. Of these, preferable are those compounds of the above formula wherein $R_4$ is a straight chain alkyl group of 3-6 carbon atoms, i.e. optically active propyl 4-hydroxy-3-methylpentanoate, butyl 4-hydroxy-3-methylpentanoate, pentyl 4-hydroxy-3-methylpentanoate and hexyl 4-hydroxy-3-methylpentanoate.

As the third type, there are mentioned those optically active dichiral secondary alcohols III wherein $Q_3$ is a

ester group.

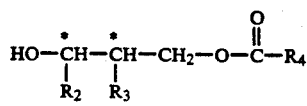

($R_2$ and $R_3$ are independently a lower alkyl group of 1-3 carbon atoms and $R_4$ is a straight chain or branched chain alkyl group of 1-10 carbon atoms.)

As typical examples of the third type, there are compounds of the above formula wherein $R_2$ and $R_3$ are both $CH_3$, i.e. optically active 3-hydroxy-2-methylbutyl esters.

These compounds, when $R_4$ is a straight chain alkyl group of 1-10 carbon atoms, specifically include optically active 3-hydroxy-2-methylbutyl acetate, optically active 3-hydroxy-2-methylbutyl propionate, optically active 3-hydroxy-2-methylbutyl butyrate, optically active 3-hydroxy-2-methylbutyl pentanoate, optically active 3-hydroxy-2-methylbutyl hexanoate, optically active 3-hydroxy-2-methylbutyl heptanoate, optically active 3-hydroxy-2-methylbutyl octanoate, optically active 3-hydroxy-2-methylbutyl 4-nonanoate, optically active 3-hydroxy-2-methylbutyl decanoate and optically active 3-hydroxy-2-methylbutyl undecanoate. When $R_4$ is a branched chain alkyl group of 1-10 carbon atoms, there are specifically mentioned optically active 3-hydroxy-2-methylbutyl 2-methylpropionate, optically active 3-hydroxy-2-methylbutyl 3-methylbutyrate, optically active 3-hydroxy-2-methylbutyl 2,2-dimethylpropionate, etc.

The carboxylic acid, which is a raw material of the skeletal portion of the optically active compounds I of the present invention, is represented by the general formula II, more specifically the general formulas II' and II''.

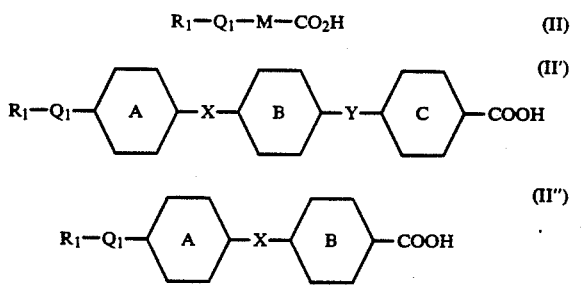

When in the formula II', $R_1$ is a straight chain or branched chain alkyl group of 3-14 carbon H atoms, $Q_1$ is a single bond or ether group, X and Y are independently a

ester group, a

ester group or a single bond, and all of

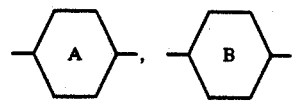

and

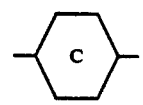

are a phenyl ring, the carboxylic acid II specifically includes 4-(4'-alkyloxy or alkyl-4-biphenylcarbonyloxy)benzoic acids, 4-(4'-alkyloxy or alkyl-4-biphenyloxycarbonyl)benzoic acids, 4'-(4-alkyloxy or alkylphenylcarbonyloxy)-4-biphenylcarboxylic acids, 4'-(4-alkyloxy or alkylphenyloxycarbonyl)-4-biphenylcarboxylic acids, 4-{4-[4-(alkyloxy or alkyl)-phenylcarbonyloxy] phenylcarbonyloxy}benzoic acids, 4-{4-[4-( alkyloxy or alkyl )phenyloxycarbonyl]phenylcarbonyloxy}benzoic acids, 4-{4-[4-(alkyloxy or alkyl)-phenyloxycarbonyl]phenyloxycarbonyl}benzoic acids, 4-{4-[4-(alkyloxy or alkyl)phenylcarbonyloxy]-phenyloxycarbonyl}benzoic acids, etc. When in the formula II'' $R_1$ is a straight chain or branched chain alkyl group of 3-14 carbon atoms, $Q_1$ is a single bond or an ether group, X is a

ester group, a

ester group or a single bond, and both of

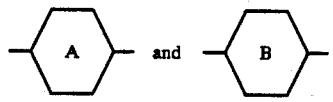

are a phenyl ring, the carboxylic acid II specifically includes 4'-alkyloxy or alkyl-4-biphenylcarboxylic acids, 4-[4-(alkyloxy or alkyl)phenylcarbonyloxy]benzoic acids and 4-[4-(alkyloxy or alkyl)phenyloxycarbonyl]-benzoic acids. As specific examples of other carboxylic acids II, there can be mentioned 4''-alkyloxy(or alkyl)-4-terphenylcarboxylic acids, 4'-(trans-4-alkyloxy or alkylcyclohexylcarbonyloxy)-4-biphenylcarboxylic acids, trans-4-(4'-alkyloxy or alkyl-4-biphenylcarbonyloxy)cyclohexanecarboxylic acids, 2-[4-(4-alkyloxy or alkylphenylcarbonyloxy)phenyl]-pyrimidinyl-5-carboxylic acids, 2-(4'-alkyloxy or alkyl-4-biphenyl )pyrimidinyl-5-carboxylic acids, 4'-(5-alkyloxy or alkylpyrimidinyl-2-oxycarbonyl)biphenyl- 4-carboxylic acids, 4'-[2-(5-alkyloxy or alkyl-2-pyridyl)ethyl]biphenyl-4-carboxylic acis, 4-[4-(trans-5-alkyloxy or alkyl-1,3-dioxane-2-yl)phenylcarbonyloxy]benzoic acids, 4'-[4-(trans- 5-alkyloxy or alkyl-1,3-dioxane-2-yl)]biphenyl-4-carboxylic acids, 2-[4-( 4-alkyloxy or alkylphenylcarbonyloxy)phenyl]pyrazinyl-5-carboxylic acids, 2-( 4 '-alkyloxy or alkyl-4-biphenyl )pyrazinyl-5-carboxylic acids, 4'-(5-alkyloxy or alkylpyrazinyl-2-oxycarbonyl)biphenyl-4-carboxylic acids and 4'-(6-alkyloxy or alkyl-3-pyridazinyl)biphenyl-4-carboxylic acids.

The alcohol or phenolic hydroxyl Compound which is another raw material of the skeletal portion of the liquid crystal compounds I of the present invention is represented by the general formula IV, more specifically the general formulas IV' and IV'''.

$$R_1-Q_1-M-OH \quad \text{(IV)}$$

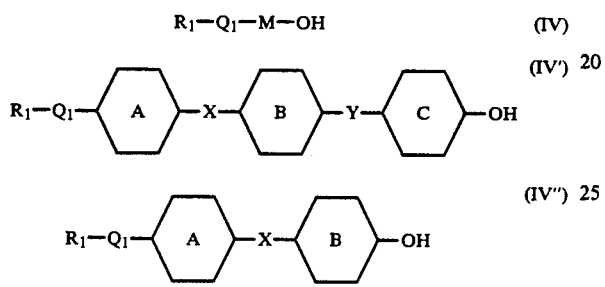

The alcohol or phenolic hydroxyl compound is an alcohol or hydroxyl derivative of the above mentioned carboxylic acid II, obtained by substituting the carboxyl group of the carboxylic acid II with a hydroxyl group. As specific examples of the alcohol or phenolic hydroxyl compound IV, there can be mentioned 4-hydroxyphenyl esters of 4'-alkyloxy or alkylbiphenyl-4-carboxylic acids, 4'-alkyloxy or alkyl-4-biphenyl esters of 4-hydroxybenzoic acids, 4'-hydroxy-4-biphenyl esters of 4-alkyloxy or alkylbenzoic acids, 4-alkyloxy or alkylphenyl esters of 4'-hydroxybiphenyl-4-carboxylic acids, 4'-hydroxy-4-biphenyl esters of trans-4-alkyloxy or alkylcyclohexanecarboxylic acids, trans-4-hydroxycyclohexyl esters of 4'-alkyloxy or alkyl-4-biphenylcarboxylic acis, 4-(5-hydroxy-2-pyrimidinyl )phenyl esters of 4-alkyloxy or alkylbenzoic acids, 2-(4'-alkyloxy or alkyl-4-biphenyl)pyrimidin-5-ols, 5-alkyloxy or alkyl-2-pyridinyl esters of 4'-hydroxy-4-biphenylcarboxylic acids, 4'-[2-(5-alkyloxy or alkyl-2-pyridyl)ethyl]biphenyl-4-ols, 4-hydroxyphenyl esters of 4-[4-(trans-5-alkyloxy or alkyl)-1,3-dioxane-2-yl ]-benzoic acids and 5-alkyloxy or 5-alkyl-2-pyrazinyl esters of 4'-hydroxy-4-biphenylcarboxylic acids.

In the above, there were listed typical examples of the carboxylic acid II and the alcohol or phenolic hydroxyl compound IV which are all a raw material of the skeletal portion of the optically active compounds I of the present invention, as well as typical examples of the optically active dichiral alcohol III which is a raw material of the optically active dichiral side chain portion of the optically active compounds I of the present invention. The optically active compounds I of the present invention can be produced by appropriately combining one raw material for the skeletal portion and one raw material for the optically active dichiral portion. The properties of the optically active compounds I are dependent upon the optically active dichiral portion, and the optically active dichiral alcohols III usable in the present invention are not restricted to those mentioned above.

The ferroelectric liquid crystal compositions obtained by incorporating an optically active compound I of the present invention have a large spontaneous polarization. The reason is presumed to be that the optically active compound I has two adjacent asymmetric carbon atoms.

The present invention is described more specifically below by way of Examples and application Example.

EXAMPLE 1

Preparation of 4-octyloxyphenyl ester of 4'-[(1R, 2S)-3-methoxy-1,2-dimethylpropoxy ]-4-biphenylcarboxylic acid (a compound of the general formula I' wherein $R_1$ is $n-C_8H_{17}$, all of $R_2$, $R_3$ and $R_4$ are $CH_3$, all of $Q_1$, $Q_2$ and $Q_3$ are —O—, X is

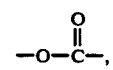

Y is a single bond, and all of

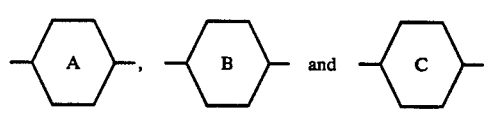

are

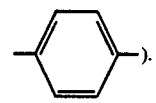

i) Preparation of (2S,3S)-4-methoxy-3-methyl-2-butanol

This compound was prepared according to the following scheme.

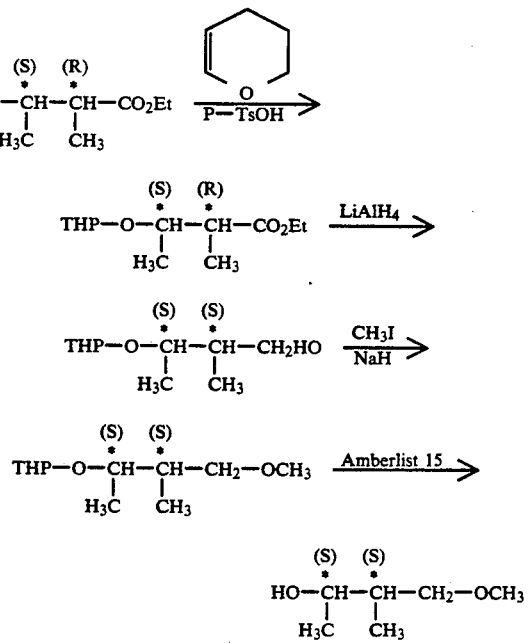

The starting material, i.e. ethyl ester of (2R,3S)-3-hydroxy-2-methylbutyric acid can be obtained by a known method [R. W. Hoffman et al., Chem. Ber., 114, 2786 (1981)]. In this method, ethyl ester of 2-methyl-3-oxobutyric acid was subjected to asymmetric reduction using baker's yeast, whereby the desired compound and its diastereometer, i.e. ethyl ester of (2S,3S)-3-hydroxylbutyric acid was obtained at a ratio of 82:18 to 87:13. In the following, the mixture of these two compounds was used, and the final product obtained by condensing the mixture with a skeletal compound was subjected to purification procedures such as column chromatography, recrystallization and the like to obtain a single diastereomer.

That is, 20.0 g of a crude product containing ethyl ester of (2R,3S)-3-hydroxy-2-methylbutyric acid as a major component and 12.7 g of 3,4-dihydro-α-pyran were dissolved in 50 ml of chloroform. To the solution was added 20 mg of p-toluenesulfonic acid (P-T₅OH) with ice-cooling. The mixture was stirred for 7 hours with ice-cooling. The reaction mixture was washed with a saturated aqueous sodium bicarbonate. The organic layer was dried and concentrated.

The residue was purified by column chromatography [silica gel, developing solvent: n-hexane-ethyl acetate (9:1)] to obtain 22.0 g of ethyl ester of (2R,3S)-2-methyl-3-(2-tetrahydropyranyloxy)butyric acid. The compound was dissolved in 200 ml of ether. To the solution was added 2.47 g of lithium aluminum hydride in small portions with ice-cooling. The mixture was stirred for 5 hours with ice-cooling. To the reaction mixture were added water, a 15% aqueous sodium hydroxide solution and water in this order. The resulting insoluble materials were removed by filtration. The filtrate was concentrated under reduced pressure to obtain 17.0 g of (2S,3S)-2-methyl-3-(2-tetrahydropyranyloxy)butanol.

7.0 g of this compound and 26.4 g of methyl iodide were dissolved in 50 ml of N,N-dimethylformamide. Thereto was added 1.64 g of oily sodium hydride (about 60%) in small portions with ice-cooling. The mixture was stirred for 2 hours with ice-cooling. The reaction mixture was poured into 200 ml of ethyl acetate, and the resulting mixture was stirred.

The insoluble materials were removed by filtration, and the filtrate was washed with water three times. The organic layer was dried and concentrated. The residue was subjected to Kugelrohr distillation under reduced pressure to obtain 6.03 g of (2S,3S)-4-methoxy-3-methyl-2-( 2-tetrahydropyranyloxy)butane. This compound was dissolved in 150 ml of methanol. Thereto was added 6.0 g of a non-aqueous strongly acidic cation exchange resin (Amberlist 15). The mixture was stirred for 2 hours at room temperature. The cation exchange resin used was removed by filtration. The filtrate was concentrated and the residue was subjected to reduced distillation (b.p. 56°–58° C./23 mmHg) to obtain 2.54 g of (2S, 3S )-4-methoxy-3-methyl-2-butanol.

The ¹H-NMR and IR spectral data of the compound are shown below.

¹H-NMR (90 MHz, CDCl₃).

δ: 0.89 (3H, d), 1.25 (3H, d), 1.4–1.7 (1H, m) 2,68 (1H, b), 3.25–3.50 (5H, m), 3.70–4.10 (1H, m).

IR$\nu_{max}^{neat}$cm⁻¹: 3420, 1740, 1460, 1200, 1110, 1020.

ii) Condensation reaction

In 35 ml of dry tetrahydrofuran were dissolved 0.4 g of the (2S,3S)-4-methoxy-3-methyl-2-butanol prepared in i) above, 1.0 g of 4-octyloxyphenyl ester of 4'-hydroxy-4-biphenylcarboxylic acid and 1.25 g of triphenylphosphine. Thereinto was dropped 0.85 g of diethyl azodicarboxylate. The mixture was stirred for about 1 hour at room temperature and then concentrated under reduced pressure. The residue was purified by column chromatography. [silica gel, developing solvent: n-hexane-ethyl acetate (9:1)] and then recrystallized from ethyl acetate-methanol to obtain 0.25 g of the title compound.

The ¹H-NMR and IR spectral data and elemental analysis of the compound are shown below.

¹H-NMR (90 MHz, CDCl₃).

δ: 1.00 (3H, t), 1.04 (3H, d), 1.09–1.50 (13H, m), 1.60–2.0 (2H, m), 1.90–2.40 (1H, m), 3.25–3.60 (5H, m), 4.00 (2H, t), 4.53 (1H, td), 6.89–8.28 (12H, m).

IR$\nu_{max}^{KBr}$cm⁻¹: 1740, 1610, 1520, 830, 770.

Elemental analysis

Calcd. for $C_{33}H_{42}O_5$: C, 76.42; H, 8.16. Found :C, 76.59; H, 8.26.

EXAMPLE 2

Preparation of 4'-[(1R,2S)-3-methoxy-1,2-dimethylpropoxy]-4-biphenyl ester of 4-octyloxybenzoic acid (a compound of the general formula I' in which $R_1$ is n-$C_8H_{17}$, all of $R_2$, $R_3$ and $R_4$ are $CH_3$, all of $Q_1$, $Q_2$ and $Q_3$ are —O—, X is

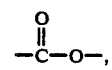

Y is a single bond and all of

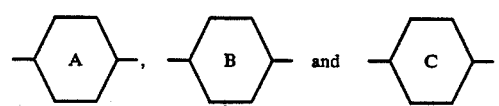

are

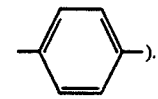

The same procedure as in Example 1 ii) was carried out using 0.4 g of the (2S,3S)-4-methoxy-3-methyl-2-butanol obtained in Example 1 i) and 1.0 g of 4'-hydroxy-4-biphenyl ester of 4-octyloxybenzoic acid, to obtain 71 mg of the title compound.

The elemental analysis of the compound are shown below.

Elemental analysis Calcd. for $C_{33}H_{42}O_5$: C, 76.42; H, 8.16. Found : C, 76.56; H, 8.26.

EXAMPLE 3

Preparation of 4'-octyloxy-4-bipheny ester of 4-[(1R, 2S)-3-methoxy-1,2-dimethylpropoxy]benzoic acid (a compound of the general formula I' wherein $R_1$ is n-$C_8H_{17}$, all of $R_2$, $R_3$ and $R_4$ are $CH_3$, all of $Q_1$, $Q_2$ and $Q_3$ are —O—, X is a single bond, Y is

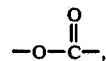

and

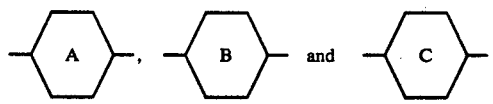

are

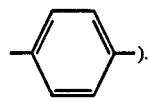

The same procedure as in Example 1 ii) was carried out using 0.4 g of the (2S,3S)-4-methoxy-3-methyl-2-butanol prepared in Example 1 i) and 1.0 g of 4'-octyloxy-4-biphenyl ester of 4-hydroxybenzoic acid, to obtain 0.50 g of the title compound.

The elemental analysis of the compound are shown below.

Elemental analysis Calcd. for $C_{33}H_{42}O_5$: C, 76.42; H, 8.16. Found :C, 76.39; H, 8.21.

EXAMPLE 4

Preparation of 4-octyloxyphenyl ester of 4-[(1R, 3S)-3-methoxy-1,2-dimethylpropoxy]-benzoic acid (a compound of the general formula I" wherein $R_1$ is n-$C_8H_{17}$, $R_2$, $R_3$ and $R_4$ are $CH_3$, all of $Q_1$, $Q_2$ and $Q_3$ are —O—, X is

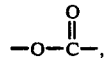

and both of

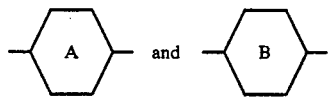

and

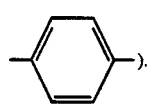

The same procedure as in Example 1 ii) was carried out using 0.45 g of the (2S,3S)-4-methoxy-3-methyl-2-butanol obtained in Example 1 i) and 1.0 g of 4-octyloxyphenyl ester of 4-hydroxybenzoic acid, to obtain 0.34 g of the title compound.

The elemental analysis of the compound are shown below.

Elemental analysis
Calcd. for $C_{27}H_{38}O_5$: C, 73.27; H, 8.65. Found : C, 73.55; H, 8.72.

EXAMPLE 5

Preparation of 4-[(1R,2S)-3-methoxy-1,2-dimethylpropoxy]-4'-(4-octyloxybenzyloxy )-biphenyl (a compound of the general formula I' wherein $R_1$ is n-$C_8H_{17}$, all of $R_2$, $R_3$ and $R_4$ are $CH_3$, all of $Q_1$, $Q_2$ and $Q_3$ are —O—, X is —$CH_2O$—, Y is a single bond, and all of The same procedure as in Example 1 ii) was carried out using 0.28 g of the (2S,3S)-4-methoxy-3-methyl-2-butanol obtained in Example 1 i) and 0.8 g of 4-hydroxy-4'-(4-octyloxybenzyloxy)biphenyl, to obtain 70 mg of the title compound.

The elemental analysis of the compound are shown below.

Elemental analysis Calcd. for $C_{33}H_{44}O_4$: C, 78.53; H, 8.79. Found :C, 78.49; H, 8.68.

EXAMPLE 6

Preparation of 4-octyloxyphenyl ester of 4'-[(1R,3S)-3-butoxy-1,2-dimethylpropoxy]-4-biphenylcarboxylic acid (a compound of the general formula I' wherein $R_1$ is n-$C_8H_{17}$ both of $R_2$, $R_3$ are $CH_3$, $R_4$ is n-$C_4H_9$, all of $Q_1$, $Q_2$ and $Q_3$ are —O—, X is

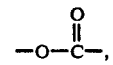

Y is a single bond, and all of

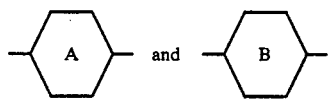

and

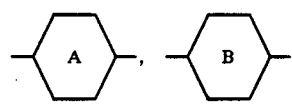

i) Preparation of (2S,3S)-4-butoxy-3-methyl-2-butanol
This compound can be prepared according to the following scheme.

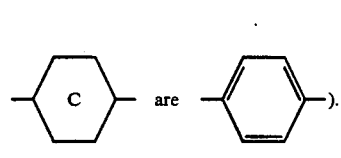

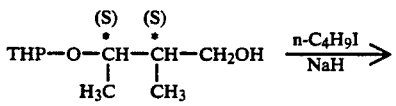

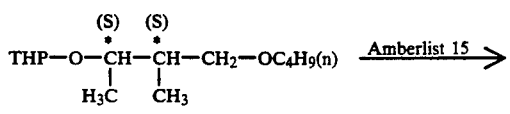

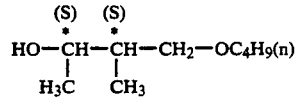

In 40 ml of N,N-dimethylformamide were dissolved 5.0 g of the (2S,3S)-2-methyl-3-(2-tetrahydropyranyloxy)butanol obtained in Example 1 i) and 24.5 g of butyl iodide. Thereto was added 1.22 g of oily sodium hydride (about 60%) in small portions with ice-cooling. The mixture was stirred for 2 hours with ice-cooling. The reaction mixture was poured into 300 ml of ethyl acetate and the resulting mixture was stirred. The insoluble materials were removed by filtration. The filtrate was washed with water three times. The organic layer was dried and concentrated. The residue, i.e. crude (2S,3S)-4-butoxy-3-methyl-2-(2-tetrahydropyranyloxy)-butane was dissolved in 150 ml of methanol. To the solution was added 6.0 g of a nonaqueous strongly acidic cation exchange resin (Amberlist 15), and the mixture was stirred for 6 hours at room temperature. The cation exchange resin used was removed by filtration and the filtrate was concentrated. The residue was subjected to Kugelrohr distillation under reduced pressure to obtain 2.54 g of ( 2S, 3S )-4-butoxy-3-methyl-2-butanol.

The 1H-NMR data of the compound are shown below.

$^1$H-NMR (90 MHz, CDCl$_3$).

δ: 0.80–0.98 (6H, m), 1.12–1.24 (5H, m), 1.40–1.95 (3H, m), 2.38 (1H, b), 3,35–3.42 (4H, m), 3.80–4.15 (m, 1H).

ii ) Condensation reaction

The same procedure as in Example 1 ii) was carried out using 0.5 g of the (2S,3S)-4-butoxy-3-methyl-2-butanol obtained in i) above and 1.0 g of 4-octyloxyphenyl ester of 4'-hydroxy-4-biphenylcarboxylic acid, to obtain 0.21 g of the title compound.

The $^1$H-NMR and IR spectral data and elemental analysis of the compound are shown below.

$^1$H-NMR (90 MHz, CDCl$_3$).

δ: 0.83–1.09 (9H, m), 1.25–1.60 (15H, m), 1.60–1.92 (4H, m), 1.95–2.30 (1H, m), 3.42 (2H, d), 3.40 (2H, t), 3.96 (2H, t), 4.25–4.70 (1H, m), 6.86–8.25 (12H, m).

IR$\nu_{max}^{KBr}$cm$^{-1}$: 1740, 1610, 1515.

Elemental analysis Calcd. for C$_{36}$H$_{48}$O$_5$: C, 77.11; H, 8.63. Found :C, 77.26; H, 8.55.

EXAMPLE 7

Preparation of 4'-octyloxy-4-biphenyl ester of 4[(1R,2S)-3-butoxy-1,2-dimethylpropoxy]-benzoic acid (a compound of the general formula I' wherein R$_1$ is n-C$_8$H$_{17}$, both of R$_2$ and R$_3$ are CH$_3$, R$_4$ is n-C$_4$H$_9$, all of Q$_1$, Q$_2$ and Q$_3$ are —O—, x is a single bond, Y is

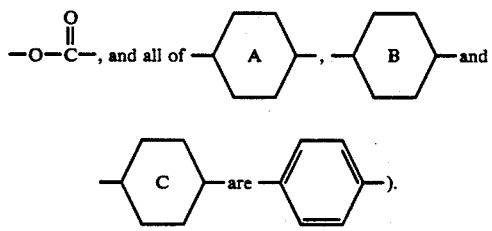

The same procedure as in Example 1 ii) was carried out using 0.4 g of the (2S,3S)-4-butoxy-3-methyl-2-butanol obtained in Example 6 i) and 1.0 g of 4'-octyloxy-4-biphenyl ester of 4-hydroxybenzoic acid, to obtain 0.25 g of the title compound.

The elemental analysis of the compound is shown below.

Elemental analysis Calcd. for C$_{36}$H$_{48}$O$_5$: C, 77.11; H, 8.63. Found : C, 77.15; H, 8.60.

EXAMPLE 8

Preparation of (1R,2S)-3-butoxy-1,2-dimethylpropyl ester of 4'-(4-transpentylcyclohexyl)-4-biphenylcarboxylic acid (a compound of the general formula I' wherein R$_1$ is n-C$_8$H$_{11}$, both of R$_2$ and R$_3$ are CH$_3$, R$_4$ is n-C$_4$H$_9$, all of Q$_1$, X and Y are a

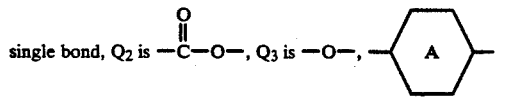

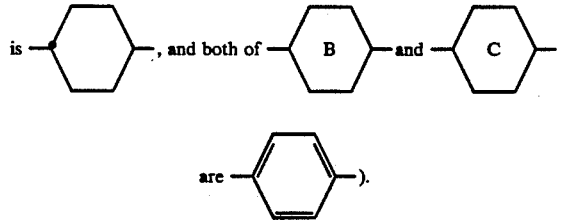

The same procedure as in Example 1 ii) was carried out using 0.55 g of the (2S,3S)-4-butoxy-3-methyl-2-butanol obtained in Example 6 i) and 1.0 g of 4'-(4-transpentylcyclohexyl)-4-biphenylcarboxylic acid, to obtain 0.18 g of the title compound.

EXAMPLE 9

The same reaction scheme as in Example 1 i) was repeated except that propyl iodide was used in place of methyl iodide, to obtain ( 2S, 3S )-4-propoxy-3-methyl-2-butanol. Then, this compound and 4-octylphenyl ester of 4'-hydroxy-4-biphenylcarboxylic acid were subjected to a condensation reaction to obtain a compound of Example 9.

EXAMPLE 10

The (2S,3R)-4-butoxy-3-methyl-2-butanol obtained in Reference Example 1 and a corresponding skeletal compound were subjected to a condensation reaction to obtain a compound of Example 10.

EXAMPLE 11–18

The (2S,3S)-4-butoxy-3-methyl-2-butanol obtained in Example 6 i) and corresponding skeletal compounds were subjected to a condensation reaction to obtain compounds of Examples 11–18.

EXAMPLE 19 AND 20

The optically active dichiral secondary alcohols obtained in Reference Example 2 or 3 and corresponding skeletal compounds, i.e. 4-octyloxyphenyl ester of 4-hydroxy-4'-biphenylcarboxylic acid were subjected to a condensation reaction to obtain compounds of Examples 19 and 20.

REFERENCE EXAMPLE 1

Preparation of (2S,3R)-4-butoxy-3-methyl-2-buytanol

The title compound was obtained by the following reaction scheme using, as a starting material, the methyl ester of (2S,3S)-3-hydroxy-2-methylbutyric acid synthesized by the method described in a literature [G. Frater et al., Tetrahedron, 40, 1269 (1984)].

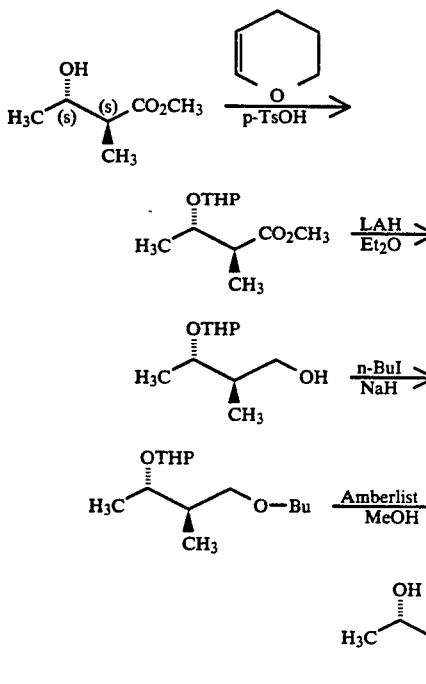

6.5 g (49.2 mmol) of methyl ester of (2S,3S)-3-hydroxy-2-methylbutyric acid was dissolved in 20 ml of CHCl₃. Thereto were added 9.2 g (0.109 mol) of 3,4-dihydro-α-pyran and 60 mg of p-TsOH.H₂O. The mixture was stirred for 2 days at room temperature. After the completion of the reaction, the reaction mixture was mixed with 20 ml of CH₂Cl₂. The resulting mixture was washed with an aqueous NaHCO₃ solution. The organic layer was dried over Na₂SO₄ and then concentrated under reduced pressure. The residue was subjected to Kugel-rohr distillation to obtain 8.64 g (yield: 81.2%) of a corresponding tetrahydropyranyl ether. 6.91 g of the compound was dissolved in 100 ml of ether, and the solution was added by small portions to a suspension containing 2.28 g (60 mmol) of lithium aluminum hydride, with ice cooling. The reaction mixture was stirred for about 1 hour at 5° C. or below. Thereto was added by small portions 60 ml of water while stirring with ice-cooling, to decompose excess lithium aluminum hydride. The ether layer was collected by decantation, dried and concentrated under reduced pressure to obtain 5.59 g (yield: 98% ) of crude ( 2R,3S)-2-methyl-3-tetrahydropyranyloxy-1-butanol as an oily material.

¹H-NMR (90 MHz, CDCl₃).

δ: 0.89–0.97 (3H, d, CH₃), 1.13–1.31 (3H, q, CH₃), 1.4–1.8 (7H, m, THP), 2.56 (1H, t, OH), 3.8 (2H, m, THP), 4.6 (2H, m, —CH₂—)

1.88 g (10 retool) of the crude (2R,3S)-2-methyl-3-tetrahydropyranyloxy-1-butanol was dissolved in 30 ml of DMF. Thereto was added 18.4 g of n-BuI. Thereto was further added carefully by small portions 4 g of oily sodium hydride (about 60%), with ice cooling. To the reaction mixture was added 300 ml of ethyl acetate. The insoluble materials were removed by filtration. The filtrate was washed with two 100 ml-portions of water, dried and concentrated under reduced pressure to obtain crude 1-butoxy-2-methyl-3-tetrahydropyranyloxybutane as an oily material. This crude product was dissolved in 150 ml of methanol. 5 g of Amberlist 15 was added thereto, and the mixture was stirred for 2 days at room temperature. The Amberlist 15 was removed by filtration and the filtrate was concentrated under reduced pressure. The residue was subjected to Kugel-rohr distillation to obtain 0.90 g of the title compound as an oily material.

Boiling point: 220°–250°/5 mmHg.

¹H-NMR (90 MHz, CDCl₃ ).

δ: 0.795–0.983 (6H, m, CH₃), 1.13–1.20 (3H, CH₃), 1.3–1.6 (4H, m, —CH₂—), 1.7–1.9 (1H, m, CH), 2.87–2.95 (1H, d, OH), 3.3–3.5 (4H, m, —CH₂—), 3.43–3.8 (1H, m, CH)

REFERENCE EXAMPLE 2

Preparation of (2S 3S)-4-butyryloxy-3-methyl-2-butanol

The title compound was obtained by the following reaction scheme using, as a starting material, the (2S,3S)-2-methyl-3-tetrahydropyranyloxybutanol obtained in Example 1 as an intermediate.

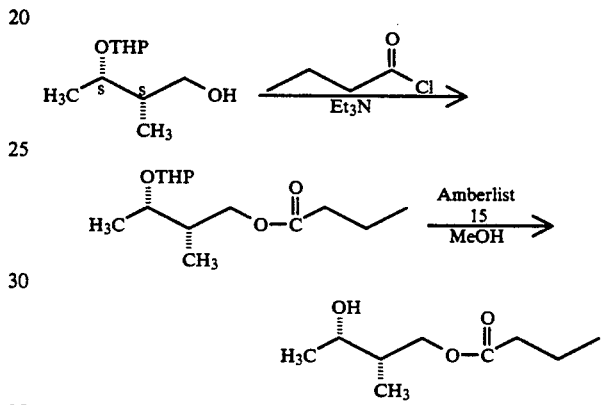

3.76 g (0.02 tool) of (2S,3S)-2-methyl-3-tetrahydropyranyloxybutanol was dissolved in 30 ml of pyridine. Thereto was dropwise added 2.56 g (0.024 mol) of butyryl chloride at room temperature. The mixture was stirred for 30 minutes at room temperature. 2 N hydrochloric acid was added to the reaction mixture. The mixture was extracted with ether. The ether layer was washed with water, dried over MgSO₄ and concentrated under reduced pressure. The residue was subjected to purification by chromatography to obtain 3.70 g (yield: 71.7%) of a desired compound. 3.40 g (0.013 mol) of the compound was dissolved in 50 ml of methanol. Thereto was added 10 g of Amberlist 15. The mixture was stirred overnight at room temperature. The Amberlist 15 was removed by filtration and the filtrate was concentrated under reduced pressure. The residue was subjected to purification by silica gel column chromatography (developing solvent: chloroform) to obtain 1.51 g (yield: 66.8%) of the title compound.

REFERENCE EXAMPLE 3

Preparation of (2S 3S)-3-methyl-4-decyloxy-2-butanol

The title compound was obtained by the following reaction scheme using a benzyl group in place of the protective group (2-tetrahydropyranyl group) used in Example 1.

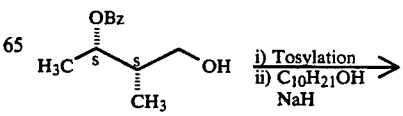

-continued

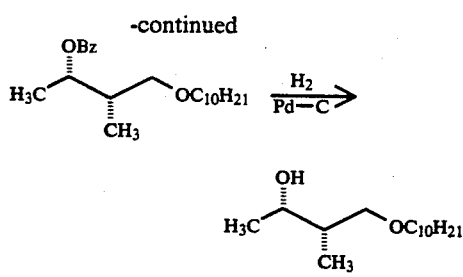

11.6 g (0.06 mol) of (2S,3S)-3-benzyloxy-2-methylbutanol as a raw material compound was dissolved in 70 ml of pyridine. 12.6 g (0.066 mol) of tosyl chloride was added thereto by small portions at room temperature with stirring. The mixture was stirred overnight at room temperature. The pyridine was removed by distillation under reduced pressure. The residue was subjected to purification by silica gel column chromatography (developing solvent: chloroform) to obtain 17.2 g (yield: 82.4%) of a desired compound, i.e. (2S,3S)-3-benzyloxy-2-methyl-1-tosyloxybutane.

0.41 g (10.26 mmol) of oily sodium hydride (about 60%) was washed with n-hexane twice. Thereto was added 20 ml of DMSO. Then, 1.35 g (8.6 mmol) of n-decyl alcohol was added by small portions. The mixture was stirred for 1 hour at 60° C. The reaction mixture was returned to room temperature, and thereto was added by small portions 2.0 g (5.7 mmol) of the (2S,3S)-3-benzyloxy-2-methyl-1-tosyloxybutane obtained above. After the completion of the dropwise addition, the mixture was stirred for 1 hour at 60° C. After cooling, the reaction mixture was mixed with water and extracted with ether. The extract was dried over $MgSO_4$ and then concentrated under reduced pressure. The residue was subjected to purification by silica gel column chromatography (developing solvent: chloroform) to obtain 0.80 g (yield: 42%) of a desired compound, i.e. (2S,3S)-3-benzyloxy-1-decyloxy-2-methylbutane. 0.80 g (2.4 mmol) of this compound was dissolved in 10 ml of ethanol containing 1 ml of 2 N hydrochloric acid. To the solution was added 0.1 g of 5% Pd-C, and the mixture was subjected to catalytic hydrogenation at room temperature under atmospheric pressure. After the reaction, the catalyst was removed by filtration and the filtrate was concentrated under reduced pressure. The residue was subjected to Kugelrohr distillation to obtain quantitatively 0.58 g of the title compound having a boiling point of 230° C./20 mmHg.

The phase transition temperatures of the compounds synthesized in the above Examples are shown in Table 1.

In Table 1, K denotes a crystalline phase; Sc* denotes a chiral smectic C phase; $S_A$ denotes a smectic A phase; N* denotes a chiral nemahic phase; Iso denotes an isotropic phase; S denotes an unidentified smectic phase. The mark ← denotes phase transition during cooling. The values of spontaneous polarization are those at a temperature lower by 10° C. than the phase transition temperature of SC*-SA (N).

TABLE 1

| Example No. | Chemical structure | Phases and phase transition temperatures (°C.) | Spontaneous polarization (nC/cm²) | Empirical formula | Elemental analysis Calculated Found |
|---|---|---|---|---|---|
| 1 | n-C₈H₁₇O–⟨⟩–⟨⟩–C(=O)O–⟨⟩–O–CH(R)*–CH(S)*–CH₂OCH₃ with CH₃, CH₃ | K →16.4← Sc* →59.5← N* →89.7← Iso; ←61.7← | 82 | | |
| 2 | n-C₈H₁₇O–⟨⟩–⟨⟩–C(=O)O–⟨⟩–O–CH(R)*–CH(S)*–CH₂OCH₃ with CH₃, CH₃ | K →60.2← S₁ →80.8← N* →99.4← Iso | Not determined | | |
| 3 | n-C₈H₁₇O–⟨⟩–C(=O)O–⟨⟩–⟨⟩–O–CH(R)*–CH(S)*–CH₂OCH₃ with CH₃, CH₃ | K →47.6← S₁ →62.5← Sc* →72.3← N* →95.2← Iso; ←67.1← | Not determined | | |
| 4 | n-C₈H₁₇O–⟨⟩–⟨⟩–⟨⟩–O–CH(R)*–CH(S)*–CH₂OCH₃ with CH₃, CH₃ | K →–12.7← Iso; ←19.2← | Not determined | | |
| 5 | n-C₈H₁₇O–⟨⟩–⟨⟩–CH₂O–⟨⟩–O–CH(R)*–CH(S)*–CH₂OCH₃ with CH₃, CH₃ | K →46.3← S₁ →72← Sc* →97.1-104.4← Iso; ←64.9← S₂ | 35.5 | | |
| 6 | n-C₈H₁₇O–⟨⟩–⟨⟩–C(=O)O–⟨⟩–O–CH(R)*–CH(S)*–CH₂OC₄H₉(n) with CH₃, CH₃ | K →18.4← Sc* →71.8← N* →86.4← Iso; ←42.4← | 60.3 | | |
| 7 | n-C₈H₁₇O–⟨⟩–⟨⟩–C(=O)O–⟨⟩–O–CH(R)*–CH(S)*–CH₂OC₄H₉(n) with CH₃, CH₃ | K →47.4← S →67.5← Sc* →72.4← N* →83.1← Iso; ←56.3← | Not determined | | |
| 8 | n-C₅H₁₇–⟨cyclohexyl⟩–⟨⟩–⟨⟩–C(=O)O–CH(R)*–CH(S)*–CH₂OC₄H₉(n) with CH₃, CH₃ | K →55.8← S_A →Iso | Not determined | C₃₃H₄₈O₃ | C, 80.44; H, 9.82 C, 80.69; H, 10.00 |

TABLE 1-continued

| Example No. | Chemical structure | Phases and phase transition temperatures (°C.) | Spontaneous polarization (nC/cm²) | Empirical formula | Elemental analysis Calculated Found |
|---|---|---|---|---|---|
| 9 | n-C₈H₁₇—⌬—O—C(=O)—⌬—⌬—O—*CH(CH₃)—*CH(CH₃)—CH₂—OC₃H₇(n)*¹  (R)(S) | K $\xrightarrow[35.1]{11.1}$ Sc* $\xrightarrow{19.7}$ N* $\xrightarrow{32.7}$ Iso | Not determined | C₃₅H₄₆O₄ | C, 79.21; H, 8.74<br>C, 79.17; H, 8.95 |
| 10 | n-C₈H₁₇—⌬—O—C(=O)—⌬—⌬—O—*CH(CH₃)—*CH(CH₃)—CH₂—O—C₄H₉(n)  (R)(R) | K $\xrightarrow[68.5]{46.5}$ Sc* $\xrightarrow{105.9}$ S_A $\xrightarrow{113.9}$ N* $\xrightarrow{134.2}$ Iso | 17.5 | C₃₆H₄₈O₅ | C, 77.11; H, 8.63<br>C, 77.24; H, 8.43 |
| 11 | n-C₈H₁₇—⌬—⌬—O—*CH(CH₃)—*CH(CH₃)—CH₂—O—C₄H₉(n)  (R)(S) | K $\xrightarrow[22.5]{15.1}$ Iso | Not determined | C₂₉H₄₄O₃ | C, 79.04; H, 10.06<br>C, 79.22; H, 10.09 |
| 12 | n-C₁₄H₂₉—⌬—O—C(=O)—⌬—⌬—O—*CH(CH₃)—*CH(CH₃)—CH₂—O—C₄H₉(n)  (R)(S) | K $\xrightarrow[66.7]{58.1}$ Sc* $\xrightarrow{72.8}$ N* $\xrightarrow{77.5}$ Iso | 32.6 | C₄₂H₆₀O₅ | C, 78.22; H, 9.38<br>C, 78.35; H, 9.53 |
| 13 | n-C₈H₁₇—⌬—O—C(=O)—⌬—⌬—O—*CH(CH₃)—*CH(CH₃)—CH₂—O—C₄H₉(n)  (R)(S) | K $\xrightarrow[0.6\sim19]{7.6\sim}$ Iso | Not determined | C₃₀H₄₄O₄ | C, 76.88; H, 9.46<br>C, 76.62; H, 9.71 |
| 14 | n-C₈H₁₇—⌬—O—C(=O)—⌬—⌬—O—*CH(CH₃)—*CH(CH₃)—CH₂—O—C₄H₉(n)  (R)(S) | K $\xrightarrow[-8.8]{-27.0}$ Iso | Not determined | C₃₀H₄₄O₅ | C, 74.34; H, 9.15<br>C, 74.37; H, 8.98 |
| 15 | n-C₈H₁₇—⌬—O—C(=O)—⌬—⌬—O—*CH(CH₃)—*CH(CH₃)—CH₂—O—C₄H₉(n)  (R)(S) | K $\xrightarrow[28.8]{8.1}$ S₁ $\xrightarrow{14.3}$ Sc* $\xrightarrow{25.7}$ N* $\xrightarrow{37.9}$ Iso | 45.4 | C₃₆H₄₈O₄ | C, 79.37; H, 8.88<br>C, 79.41; H, 8.95 |
| 16 | n-C₈H₁₇—⌬—O—⌬—⌬—C(=O)—O—*CH(CH₃)—*CH(CH₃)—CH₂—O—C₄H₉(n)  (S) | K $\xrightarrow[30.1]{21.1}$ Iso | Not determined | C₃₀H₄₄O₄ | C, 76.88; H, 9.46<br>C, 77.00; H, 9.50 |

TABLE 1-continued

| Example No. | Chemical structure | Phases and phase transition temperatures (°C.) | Spontaneous polarization (nC/cm²) | Empirical formula | Elemental analysis Calculated Found |
|---|---|---|---|---|---|
| 17 | n-C₈H₁₇-[pyrazine]-[phenyl]-O-CH(R)*-CH(S)*-CH₂-O-C₄H₉ (CH₃, CH₃) | — | Not determined | C₂₇H₄₂N₂O₂ | — |
| 18 | n-C₈H₁₇O-[phenyl]-C(=O)-O-[phenyl]-[phenyl]-O-C(=O)-CH(R)*-O-CH(S)*-CH₂-O-CH(S)*-CH₂-CH₃ (CH₃, CH₃) | K —35.2→ Sc* ←31.7— N* ←35.2— Iso | Not determined | C₃₇H₄₈O₆ | — |
| 19 | n-C₈H₁₇O-[phenyl]-C(=O)-O-[phenyl]-[phenyl]-O-CH(R)*-CH(S)*-CH₂-OC(=O)C₃H₇(n)*² (CH₃, CH₃) | K ⇌(20.1/47.3) S₁ ⇌(55.2) Sc* ⇌71.7 N* ⇌93.7 Iso | 74.5 | C₃₆H₄₆O₆ | C, 75.23; H, 8.07 C, 75.10; H, 8.23 |
| 20 | n-C₈H₁₇O-[phenyl]-C(=O)-O-[phenyl]-[phenyl]-O-CH(R)*-CH(S)*-CH₂-OC₁₀H₂₁(n)*³ (CH₃, CH₃) | K ⇌(14.1/28.8) Sc* ⇌56.6 N* ⇌65.7 Iso | 35.0 | C₄₂H₆₀O₅ | C, 78.22; H, 9.38 C, 78.04; H, 9.62 |

*¹⁾Reference Example 1
*²⁾Reference Example 2
*³⁾Reference Example 3

APPLICATION EXAMPLE

The optically active compounds I of the present invention shown in Table 1 were incorporated into a mother liquid crystal shown in Table 2, and the resulting compositions were measured for spontaneous polarization. The results are shown in Table 2. In Table 2, the values of spontaneous polarization are those at a temperature lower by 10° C. than the upper limit temperature of Sc* phase.

TABLE 2

| Mother liquid crystal | Optically active compound I | | Spontaneous polarization (nC/cm$^2$) |
|---|---|---|---|
| | Example No. | Amount added (wt. %) | |
| A | 1 | 10 | 8 |
| A | 1 | 20 | 17 |
| A | 1 | 30 | 25 |
| A | 6 | 10 | 7 |
| A | 6 | 20 | 15 |
| A | 6 | 30 | 22 |
| A | — | — | <1 |

Mother liquid crystal A:

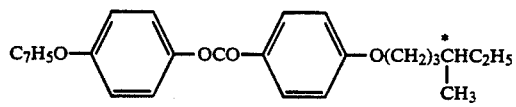

Of the liquid crystal compositions shown in Table 2, the composition shown in the uppermost column was sealed in a cell constituted by (a) two glass substrates each with a transparent electrode, obtained by spin coating of a polyimide and subsequent rubbing and (b) a spacer consisting of a polyethylene terephthalate film of 6 μm in thickness, whereby a liquid crystal device was prepared. A rectangular wave (10 Hz, 40 Vp-p) was applied to the liquid crystal device at room temperature, and the optical response was observed by a polarizing microscope. A good optical response was obtained. Meanwhile, in the case of the device prepared by using the mother liquid crystal shown in the lowermost column, no optical response was obtained even when a rectangular wave of high voltage 50 Vp-p was applied.

EXAMPLES OF COMPOSITION PREPARATION

The following liquid compositions were prepared using the compound of Example 19 or the compound of Example 12. Using these compositions, liquid crystal devices as shown in FIG. 1 were prepared. All of these devices showed a good optical response when a rectangular wave (40 Vp-p, 10 Hz) was applied at room temperature. Further, each composition was mixed with 3% by weight of an anthraquinone type or azo type dichroic dye, and guest host type liquid crystal devices were prepared in the same manner as above. All of these devices showed a good optical response of guest host type. Thus, it was found that the compounds of the present invention are useful as a component of liquid crystal compositions.

Liquid crystal composition 2

| Component | Amount (mole %) |
|---|---|
| C₆H₁₃O—⬡—OCO—⬡—⬡—OCHC₆H₁₃ (with CH₃ branch, * chiral) | 33 |
| C₈H₁₇O—⬡—⬡—CO₂CH₂CHC₂H₅ (with CH₃ branch, * chiral) | 15 |
| Compound of Example 12 | 20 |

Liquid crystal composition 3

| Component | Amount (mole %) |
|---|---|
| C₇H₁₅O—⬡—CO₂—⬡—⬡—CO₂CH₂CHC₂H₅ (with CH₃ branch, * chiral) | 15 |
| Compound of Example 19 | 25 |
| C₈H₁₇O—⬡—CO₂—⬡—OCH₂CHC₂H₅ (with CH₃ branch, * chiral) | 35 |
| C₉H₁₉O—⬡—CO₂—⬡—OCH₂CHC₂H₅ (with CH₃ branch, * chiral) | 25 |

Liquid crystal composition 4

| Component | Amount (mole %) |
|---|---|
| C₈H₁₇O—(pyrimidine)—⬡—OCH₂CHC₄H₉ (with CH₃ branch, * chiral) | 30 |
| C₁₁H₂₃O—(pyrimidine)—⬡—OCH₂CHC₂H₅ (with CH₃ branch, * chiral) | 30 |
| C₈H₁₇O—(pyrimidine)—⬡—OCOCHC₂H₅ (with CH₃ branch, * chiral) | 30 |
| Compound of Example 12 | 10 |

As is clear from Examples and Application Example, the present invention provides ferroelectric liquid crystal compounds having a very large spontaneous polarization and physical and chemical stabilities. Further, the use of these compounds as a component of liquid crystal compositions is effective to provide liquid crystal compositions with significantly improved spontaneous polarization.

What is claimed is:

1. An optically active compound exhibiting a chiral smectic C phase represented by the general formula I:

$$R_1-Q_1-M-Q_2-\overset{*}{C}H-\overset{*}{C}H-CH_2-Q_3-R_4$$
$$\phantom{R_1-Q_1-M-Q_2-}R_2\phantom{H-}R_3$$

wherein $R_1$ is an alkyl group of 3–14 carbon atoms; $R_2$ and $R_3$, which may be the same or different, are independently a lower alkyl group of 1–3 carbon atoms; $R_4$ is an alkyl group of 1–10 carbon atoms; $Q_1$ is a single bond or an ether group; $Q_2$ is an ether group or a carboxylic acid ester group and $Q_3$ is an ether group; M is

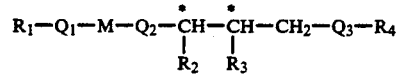

X and Y are independently a single bond, a carboxylic acid ester group or a methyleneoxy group and

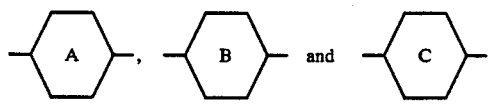

are p-phenylene groups; the carbon atoms with the asterisk (*) denote asymmetric carbon atoms.

2. An optically active compound according to claim 1, wherein Y is a single bond, X is carboxylic acid ester group having a structure of

or a methyleneoxy group having a structure of —CH$_2$O—.

3. An optically active compound according to claim 2, wherein Q$_1$ and Q$_2$ each is an ether group, X is a carboxylic acid ester group having a structure of

and Y is a single bond.

4. An optically active compound according to claim 2, wherein R$_1$ is n-C$_8$H$_{17}$, and R$_2$ and R$_3$ re methyl groups.

5. An optically active compound according to claim 4, wherein R$_4$ is a C$_4$ to C$_{10}$ alkyl group.

6. An optically active compound according to claim 5, wherein R$_4$ is n-C$_4$H$_9$.

7. An optically active compound according to claim 1, namely:

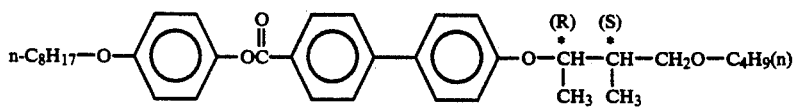

or

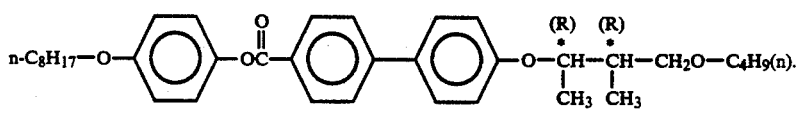

8. An optically active compound according to claim 4, wherein R$_4$ is a —CH$_3$ group.

9. An optically active compound according to claim 1, namely;

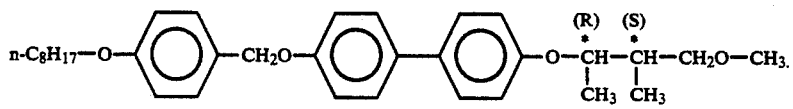

10. An optically active compound according to claim 5, wherein R$_4$ is n-C$_{10}$H$_{21}$.

11. An optically active compound according to claim 1, namely;

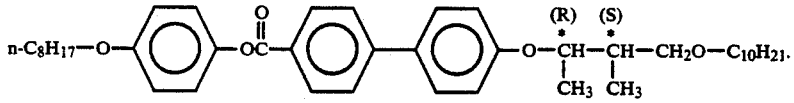

12. An optically active compound according to claim 7, namely;

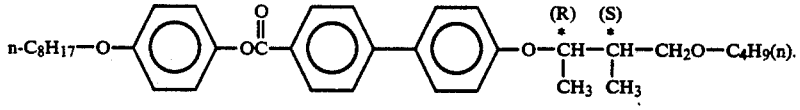

13. Optically active compounds according to claim 1, wherein one of X and Y in M is a single bond and the other is a carboxylic acid ester group, and all of

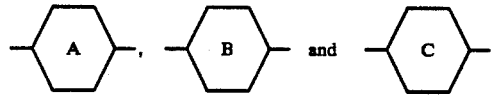

in M are p-phenylene.

14. Liquid crystal compositions comprising at least one of the optically active compounds according to claim 1.

15. Liquid crystal optical modulators using a liquid crystal composition according to claim 14.

* * * * *